United States Patent [19]
Urko

[11] Patent Number: 6,149,610
[45] Date of Patent: Nov. 21, 2000

[54] METHOD FOR MASSAGING THE NECK AND THE FACE AND DEVICE FOR REALISING THE SAME

[76] Inventor: Marina Sergeevna Urko, Leningradskoe Shosse, 24, Korp. 1, kv. 29, 125212 Moscow, Russian Federation

[21] Appl. No.: 09/194,945

[22] PCT Filed: Jul. 2, 1996

[86] PCT No.: PCT/RU96/00179

§ 371 Date: Dec. 7, 1998

§ 102(e) Date: Dec. 7, 1998

[87] PCT Pub. No.: WO98/00089

PCT Pub. Date: Aug. 1, 1998

[51] Int. Cl.[7] .................................................... A61F 13/20
[52] U.S. Cl. ................................................................ 601/15
[58] Field of Search ......................................... 601/15, 17

[56] References Cited

FOREIGN PATENT DOCUMENTS

| | | |
|---|---|---|
| 0330583A3 | 8/1989 | European Pat. Off. . |
| 2492659A1 | 4/1982 | France . |
| 3725139C1 | 9/1988 | Germany . |
| 2086222 | 8/1997 | Russian Federation . |
| 2113837 | 6/1998 | Russian Federation . |
| 1804835A1 | 3/1990 | U.S.S.R. . |
| 1782590A1 | 12/1992 | U.S.S.R. . |

OTHER PUBLICATIONS

The Handbook on Medical Cosmetology "Medicine" 1978 (Leningrad) pp. 60–66, [see Concise Explanation].

"The Methodical Recommendations on Carrying Out Hygienic Message of the Face and Neck" TsPKTB, Minbit RSFSR, 1976 pp. 1, 3–18 [see Concise Explanation].

"The Technological Instructions on Different Kinds of Cosmetic Works" TsBNTI, MINBIT RSFSR, 1979 p. 18 [see Concise Explanation].

Kolgunenko, I. I., "Lessons in Beautification", 1980, Reklama, (Kiev) pp. 14–28 [see Concise Explanation].

"Spravochnik po kosmetike" under editoship. M.A. Rozentula, 1964, izd. Meditsina, (Moscow), pp. 132–133, 216–227.

"Handbook on Medical Cosmetology" (Leningrad), Meditsina, 1978.

Kolgunenko, I. I., "Lessons in Beautification" (Kiev), Reklama, 1980.

"Methodical Recommendations on Carrying Out Message of the Face and Neck" TsPKTB, Minbyt RSFSR, 1976.

"Technological Instructions Relating to Cosmetic Techniques" TsBNTI, Minbyt RSFS, 1979.

*Primary Examiner*—Michael A. Brown
*Assistant Examiner*—Lalita M. Hamilton
*Attorney, Agent, or Firm*—Nath & Associates PLLC; Gary M. Nath; Lee Heiman

[57] ABSTRACT

The present invention relates to the field of medical cosmetology and may be used as an alternative solution to surgical removal of neck and face defects. This unique and effective method comprises applying a vibration action on the soft tissues of the face and the neck. This method may be used to make a person look generally much younger and comprises cleaning the capillaries of the skin integument and of the muscles; of the face and the neck, recovering the elasticity of the muscular and ligamental apparatus, and reducing the subcutaneous fatty layer as well as the muscular mass to a minimum acceptable level. This method sharply increases the exchange processes within a cell, for example those of a structural unit in any tissue in the organism. This massage method may be used for the non ablative removal of ageing skin, which results in natural tightening of that skin.

3 Claims, No Drawings

METHOD FOR MASSAGING THE NECK AND THE FACE AND DEVICE FOR REALISING THE SAME

FIELD OF THE INVENTION

The invention relates to the field of medical cosmetology and may be used as an alternative solution to surgical removal of face defects.

Massage is mechanical action on the tissues of an organism. Its physiological effect is due to the reflex effect on the organism: even with light surface massage, at first there is a reaction by the cutaneous ceptors, and then there is a reflex reaction by the nervous system, blood circulation, lymphopoiesis. The effectiveness of the procedure depends on the technique, the length of the action, the number of treatments.

There are different kinds of massage: 1) hygienic, wherein the object is to improve the health of the organism and provide prophylaxis against the occurrence of defects (cosmetic massage relates to this type of massage); 2) therapeutic massage (including, plastic), widely used during different illnesses; 3) sports massage, the object of which is to remove tiredness and enhance working capacity.

BACKGROUND ART

It is known that different methods of massage were already used in ancient times. In Russia, massage was first given scientific basis and used by A. I. Pospelov. Cosmetologists in our era, as a rule, use methods developed in the Moscow Scientific-Research Cosmetology Institute. ("*Handbook on Medical Cosmetology,*" Leningrad, "*Meditsina,*" 1978, pp. 60–63; I. I. Kolgunenko "*Lessons in Beautification,*" 3rd ed., Kiev, Reklama, 1980; "*Methodical Recommendations on Carrying Out Massage of the Face and Neck,*" TsPKTB, Minbyt RSFSR, 1976.)

Hygienic massage, at the base of which lies surface, measured, smooth. movements carried out in strict accordance with the direction of the massage lines, is, used in the majority of cases in the field of cosmetology. A small amount of one or another massage agent (cream or vegetable oil, for example olive oil) or talcum is preliminarily applied to the skin. The massage is carried out with light, soft, rhythmic movements, without stretching the skin. The length of one treatment of hygienic massage is 15–20 minutes, a course consists of 10–20 treatments.

Therapeutic massage is prescribed for several illnesses (neurological, skin blood circulation disturbances, disturbances of sebum isolation, acne, etc.). It is carried out, as a rule, in a more energetic manner than hygienic massage. There are several kinds of therapeutic massage: plastic, therapeutic massage according to Professor A. I. Pospelov, therapeutic massage according to Jacque.

The essence of plastic massage is deeper mechanical action on not only the skin and facial muscles, but also on subcutaneous fat, circulatory and lymphatic vessels. The aim of plastic massage is not prophylaxis but treatment of ageing.

At the base of the known method for plastic massage proposed by I. I. Kolgunenko lies strictly rhythmic, rather strong and deep pressures, with vibrations (or without vibrations), without shifting facial tissues and directed inwards and to bones. Pressure is applied taking the location and direction of massage lines into account and using talcum. The length of one session is 10–15 minutes, a course consists of from 10 to 25 treatments. It is a generally accepted practice to alternate plastic massage with, talcum with hygienic massage with cream.

Therapeutic massage according to A. I. Pospelov and Jacque acts on the subaceous glands. The aim of such a massage is to remove the contents of subaceous glands and acnes, to resorb infiltrates, to cleanse fatty and provide treatment of porous. skin. At the base of the massage according to A. I. Pospelov are stroking and pinching actions which are carried out with the tips of the thumb and index fingers of the right hand in a certain direction; this massage is performed on a dry face. Massage according to Jacque is based on strong and frequent pinches with gripping of not only the skin but also the subcutaneous fat. The movements are carried out with the thumb and index finger, taking the direction of the massage lines into account. Massage is also performed with talcum. The length of each treatment is 10 minutes, a course consists of 10–20 treatments.

It is known that all the massage methods used at present (except for the massage proposed by Kolgunenko) are directed to change the skin surfaces by improving nutrition to the skin, but are not directed to deep age changes of the muscular-ligamental apparatus. Age changes are characterized by an increase of the fatty layers in a muscle itself, by ligament calcification and strain, sagging of all the tissues and by loose skin.

DISCLOSURE OF THE INVENTION

The present method proposes reduction of the subcutaneous fatty layer to a minimum acceptable level, recovery of the elasticity of the muscular and ligamental apparatus, and, as a result, removal of excess skin, not by cutting it off, but as a result of its natural tightening. Furthermore, there is a substantial reduction of the muscle mass of the face, which results in a gradual reformation of its form, i.e. in partial rejuvenation . The actually attained effect can be compared with a "shaping" effect for the face.

In the proposed method of massage of the face and neck, in addition to the usually used elements for action on soft tissues (vibration, static action on biologically active points, stroking the surface of the skin, rubbing, kneading etc.), new elements are added, to which relate:

1) great intensity and depth of penetration until a stop is felt in the tissues of the face and neck;

2) a new, distinctive method of vibration action;

3) use of a special cream-suspension;

4) lengthy action—1 hour 20 minutes.

1. The greater part of the massage time, 60 minutes, is used for intense and deep penetration into the soft tissues of the face and neck (only 10 minutes at the beginning and end of treatment are used for surface stroking to prepare the face tissues for the intense action and to "get out" of it).

During the course of the massage, the intensity and depth of penetration into the tissues of the face and neck increase as the subcutaneous fat is burned away and ihe muscle mass reduced, and subsequently the feeling of the stop changes.

2. The new method of vibration action on the tissues consists of frequent spiral rubbing movements with the palm surface of the phalanxes of all five fingers, the palms of both hands participating in the movements. The rate of the spiral rubbing is 200–250 movements per minute (which is 3–3.5 times greater than the frequency of movement used in known methods) (see "*Methodical Recommendations on Carrying Out Hygienic Massage of the Face and Neck,*" TsPKTB, Minbyt RSFSR, 1976). Furthermore, if there are 4–8 rotating-looping movements on each massage line in the usual massage technique, in the proposed method there are 3000–4000 rotating-looping movements. The rotating-looping movements are converted into spiral movements over the whole muscle volume. Massage is carried out taking the anatomicophysiological location of the muscles and ligamental apparatus of the face and neck into account.

A slapping movement is performed with the same frequency as the spiral rubbing (i.e. 200–250 movements per minute) with the balls of the 2nd–5th fingers of the hands. Together with that movement, a slapping movement is used which is performed by the palm surface of the 2nd–5th fingers and also by the whole surface of the palm, both alternately and simultaneously with both hands. With the simultaneous dropping of the hands, the optimum frequency and amplitude of movement of the hands are selected depending on the condition of the face tissues.

The described steps (rubbing and slapping) soften the submaxillary fascia, restore elasticity thereto, visually giving the lower jaw a more sharp and youthful shape. Rubbing the cartilages of the nose makes it possible to substantially narrow the nose.

3. A special cream-suspension for the proposed massage of the face and neck includes seed or olive oil, cacao oil, lanolin, wax, vitamins A and E, citric acid and water with the following relationship of the ingredients, % by weight:

| CaCao Oil | 4–6 |
| lanolin | 3–5 |
| Beeswax | 3–4 |
| Vitamin A in Oil | 0.8–1.2 |
| Vitamin E in Oil | 0.8–1.2 |
| Citric Acid | 0.8–1.2 |
| Olive or Seed Oil | 30–50 |
| Distilled Water | balance to 100% |

The proposed cream-suspension satisfies the requirements which we require of massage cream: a high water content, a high percentage content of vegetable oils and oil-soluble vitamins, absence of an emulsifier (as an additional artificial ingredient).

It has been established as a result of studies carried out by scientists that accumulation of neutral, hard-to-remove fats in the organism results in a disturbance of the trophicity of any tissues of the organism, in a change of the metabolic processes and in ageing. When there is a large amount of such accumulations, there are crystals of calcium and fatty acids, cholesterol, present; these disturbances result in a loss of tissue elasticity, narrowing of the lumen of capillaries, their permeability is damaged, blood circulation is impaired.

Vegetable oils and acids, being natural solvents of neutral fats, substantially accelerate their solution and removal, sharply intensifying the process of restoration of metabolic processes, blood supply; i.e. the process of restoration of a cell membrane (bilipoid layer) takes place, and consequently recovery of the cell itself as a structural unit in any tissue of the organism.

For more effectiveness of the massage, in addition to the cream-suspension described above, olive or any other vegetable oil (except for sunflower oil) is applied to the skin of the face and neck. The consumption of cream and oil for one treatment exceeds the usually accepted norm by 4 times (see "Technological Instructions Relating to Cosmetic Techniques," TsBNTI, Minbyt RSFSR, 1979, page 18).

The large amount of cream and oil ensures deep penetration of the hands into all the tissues of the face and neck without shifting them.

| Established norms of consumption of cream and oil | | Proposed consumption of cream and oil | |
|---|---|---|---|
| Face | | | |
| cream | –5 g | cream | –20 g |
| oil | –7 g | oil | –25 g |
| Neck | | | |
| cream | –3 g | cream | –15 g |
| oil | –5 g | oil | –20 g |

4. The length of massage treatment, which is 1 hour 20 minutes makes the methods of action on the tissues of the face and neck as described above especially effective. Where the number of treatments with women is from 15 to 20, and in special cases to 30, and with men from 20 to 30, in some cases to 40, a stable positive cosmetic effect is attained.

The sequence in which the symptoms of visual and tactile improvements appear is as follows:

a) the subcutaneous fatty layer is reduced;

b) at first blood supply to the surface is improved and then to the deep tissues of the face and neck;

c) the fatty layers of deep tissues are narrowed;

d) the blood supply and elasticity of the ligamental apparatus of the face and neck muscles are restored;

e) the loss of fatty layers, reduction of the connective mass, reanimation of the blood supply—surface and deep—result in consolidation of the soft tissues (muscles with fascia, skin with muscle tissue); soft tissues of the face "tightly cover" the face part of the skull, creating a dense monolithic structure.

Repeated courses of massage treatment every 1–2 years results in stabilization of the achieved cosmetic effect, substantially slowing down the manifestation of ageing features of the face and helping to avoid surgery.

APPLICABILITY

The proposed method can be an alternative to surgical correction of face and neck defects and has undoubtable advantages:

1) as a biologically flowing, natural process, leading to tissue recovery, and not to tissue removal;

2) such a massage maintains the activity of the metabolic processes and full-strength blood supply to the tissues of the face and neck for a long period;

3) massage, being prophylactic, hinders the growth of subcutaneous fat and deep deposits of fat, and consequently, hinders spasm, edema, loss of elasticity of the muscle mass and ligamental apparatus and deformation of the face oval.

Contraindications to carrying out massage are:

1) acute inflammatory, infectious and virus diseases, high temperature;

2) acute illness of a facial nerve;

3) pustular skin diseases;

4) acute skin diseases (dermatitis, eczema, herpes, neurodermite et al);

5) fungus diseases;

6) flat warts;

7) hypertension in the decompensation stage.

Side effects: Eruptions in the form of small rose-colored papules are possible in the process of consolidation of soft tissues, but this is not a reason to terminate the course of massage.

PREFERRED EMBODIMENT OF THE INVENTION

Before beginning the massage, a hot compress is applied to prepare the tissues of the face and neck, the object of this being to expand the network of capillaries. Then massage agents are applied to the face and neck. The massage itself begins with light stroking movements in accordance with a known scheme (see "Technological Instructions Relating to Cosmetic Techniques," TsBNTI, Minbyt RSFSR, 1979, pp. 4–9). This is followed by frequent, spiral rubbing (until a stop is felt). The order in which these movements are carried out is the following: worked over are tissues of the neck and lower jaw; lines of the nasolabial muscles—from the chin to the bridge of the nose; tissues of the forehead, orbicular muscles of the eyes and temples; cheek muscles. The technique of carrying out spiral rubbing and slapping movements is comprehensively described above in item 2 of the instant specification—"new, distinctive method of vibration action." The intensity of these movements grows as the muscle turgor improves. From 3000 to 4000 spiral and slapping movements are used for treatment of each muscle. Surface stroking of all the muscles of the face and neck is carried out at the end of the treatment.

PREPARATION OF THE CREAM

The cream includes the following ingredients: cacao oil—5 g, lanolin—4 g, beeswax—3 g, olive or seed oil—40 g, vitamin A in oil—1 g, vitamin E in oil—1 g, citric acid—1 g, balance—distilled water.

Method of preparation. The ingredients—cacao oil, lanolin, wax, olive or seed oil are mixed and placed in a steam bath, are heated while being constantly mixed until a homogeneous mass is obtained. Then the vessel is placed in a sink with cold running water until the prepared mixture is completely cooled, preliminarily cooled distilled water and citric acid are added, and with constant mixing, a homogeneous cream-suspension is obtained. Cold distilled water and cooling the vessel in which the cream is prepared promote emulging. Oily solutions of vitamins A and E are added after the cream-suspension is obtained. Aromatic additives are introduced at the desire of the producer.

APPENDIX NO. 1

The copies of references, which are accessible to the Applicant, are presented in English. However since some of references are not considered as especially relevant in relation to the Application these references, what are not translated in English, are shown being untranslated and only parts which are relevant to disclosure the standard of techniques are translated.

<<Handbook on Medical Cosmetology>>Leningrad, <<Meditsina>>, 1978

<<The first section covers common problems and aims of the massage. Using a massage we can eliminate either totally or partially age changes in place of subcutaneous fat by this means to restore the lost face shape and oval >>(p. 60, lines 20–22).

Process of preparation of the face and neck skin includes steps of cleaning, warming and applying of one or another massage agents to it. On page 61 (lines 16–18) there are dealing with a hygienic massage and pointing that the aim of the face and neck skin massage is <<a prophylaxis against the occurence of the early skin withering. This kind of massage is the best to apply when there are not the sharply defined senile changes of the face and neck skin>>.

<<The basis for this kind of massage are surface, rhythmic, soft movements, strictly directed in accordance with the skin lines direction (p. 61, 1.24–26). <<The face skin massage is carried out in direction of lymphatic vessels. FIG. 1 shows a direction of massage lines. >>Massage (grinding) and vibration are carried out in exit points of skull-brain nerves FIG. 2,3 (p. 61, 1.32–33, 36–37). <<The duration of one hygienic massage session is 15–20 min. A course of a massage needs to begin from short sessions, what should be then little by little prolongated. For young people it will suffice to conduct a course of 10 massages by 1–2 sessions a week. For a year it will be enough to perform 1–2 such courses. For people of a mature are need conducting 15–20 sessions during 1-1,5 months and 2–3 such courses a year. In the time lapse between courses it would be well to carry out 1 session a 7–10–14 days for supporting the achieved results. We emphasize that only a full-fledged course of hygienic massage gives the desirable effect (p.62, 1.1–9).

Later on p.63, 1.4–6 we can see a description of therapeutic massage. There are several kinds of therapeutic massage: plastic, therapeutic massage according to Professor A. I. Pospelov, therapeutic massage according to Jacque.

The aim of plastic massage is not only prophylaxis, but treatment of more pronounced signs of aging>>(p.63, 64, 1.1–2). Plastic massage is recommended to people with deep wrinkles, flabbiness and facial tissues prolapsus (shifting), elasticity loss in consequence of them, face deformation, oval changes etc. (p.64,1.6–8). Usually plastic massage is mostly prescribed to people after 30–40 years old and older. Sometimes people even before this age need such kind of massage, in particularly for treatment of the fat and porous skin with reduced muscular tone (p.65, 1.1–2–3). The basis for plastic massage is rhythmic rather energetic and strong (not rough) deep pressures without shifting facial tissues and directed inward and pressing them to bones.

Pressings are carried out in dependence of situation and direction the skin lines. Plastic massage is performed by the use of dry agent-talcum>>(p.65, 1.5–10).

The length of one session is approximately 15 minutes. And in the case of plastic massage without special preparation and final actions it lasts 8–10 minutes. Per one course of treatment usually necessary to perform from 10 to 20–25 procedures in a day or 1–2 times a week>> (p.65, 1.15–17).

<<Are performed 2–3 courses a year, and on completion of the full treatment are recommended supporting the achieved result sessions (once a 7–14 days). (p. 65, 1.18–20).

Therapeutic massage according to Mr. A. I. Pospelov

<<This kind of massage acts on the subaceous glands. The aim of such a massage is to remove the contents of subaceous glands and acnes (black points). Massage according to the Mr. Pospelov's scheme cleans the fat skin well (FIG. 4). This massage is not acceptable to people suffering with acute skin diseases and more pronounced with loss of the skin elasticity. The basis for this massage are stroking and pinching movements, which are carried out with the tips of the thumb and index fingers of the right hand taking the direction pointed in FIG. 4>> (p. 66, 1.1–9).

<<Massage is carried out on a dry face, preliminarily refined with spirit >>(p.66, 1.13–14). <<The length of each session lasts about 10 minutes. These procedures are prescribed performing in a day, the course of treatment consists of 10–15 sessions in 2–3 months, in case of need it can be repeated>>(p. 66, 1.15–19).

Therapeutic massage according to Jacque.

<<The aim of this kind of massage is to resolve infiltrates (inflamed infiltrations) with pimples rash, treatment of the fat, porous skin>>(p.66, 1.20, 24–26).

At the base of the massage are strong and frequent pinches with gripping of not only the skin, but also the subcutaneous cellular. The movements are carried out with the thumb and index fingers taking the direction of the massage lines (p.66, 1.26–31). <<Massage is performed with talcum.>>(p. 66, 1.37). <<The massage duration is 6–8 minutes. The first 5 sessions are performed daily, then in a day or 2–3 times a week. The complete course of this treatment consists of 10–15 to 20 sessions (p.66, 1.43–45).

The Section:>> Methodical Recommendations on Carrying Out Massage of the Face and Neck>> TsPKTB, Minbyt RSFSR, 1976 and <<The Technologic Instruction Relating to Cosmetic Techniques>>, TsBNTI, Minbyt RSFSR, 1979. The methodical recommendations (title—page, 1.1–4) and technologic instructions intended for people who perform cosmetic massage.

There are given description of the method of hygienic massage of the face and neck skin. In those instructions are stated the process of performance of cosmetic treatment: hygienic (cosmetic) massage of the face and neck (this description in the Section "Cosmetic massage" totally agrees with above- mentioned description in "The Methodical Recommendations"). On p. 18 are given rates of working expenses (cream, oil etc.) per one treatment named "hygienic massage of the face and neck".

Then there are given the requirements on execution of other cosmetic treatment, that is not concerning to the present Application materials.

Now we consider some aspects of "The Methodical Recommendations". There are described the essence of cosmetic massage on page 3, 1.7–9, 10. <<Is recommended to perform massage with treatment by 15–20 sessions with duration of 15 minutes every one in a day. The whole treatment is repeated twice a year, in breaks between the treatment courses massage is carried out 3–4 times a month.>>

The physiological action of massage is described on p.4. The technique of massage is given on p.5, 1.14–15.>>During the massage is not recommended to touch the client's eyelashes, nose, ears, thyroid gland <<.

<<Movements should be soft, sliding, slightly pressing but not stretching and shifting the skin. Movements are performed on the massage lines four or eight time (p.5, 1.13–11). >>The technique of the massage includes 5 main modes: stroking, grinding kneading and slapping >>(p 5, 1.3–4).

<<Grinding>>—is carried out with the palm surface of the phalanxes of fingers or back surface of the middle phalanxes of 2–5 fingers, folded in fist>>(p.6, 1.4–6).

<<Slapping>>—is carried out with moving fingers of the both hands simultaneously, and at the same time the masseuses' hands, has been touched the massaging place immediately are removed from it. Thus the movement takes a character of separate following one after another pushes. These movements are performed with the palm surface of all fingers>> (p. 6, 1.21–26).

<< All movements on the face skin are carried out at the oral time 4, strictly rhythmically.>>(p. 6–7,1.35, 1).

The technique of the massage is shown on pages 7–18.

In <<Technological Instruction Relating to cosmetic techniques>>, TsBNTI, Minbyt RSFSR, 1979, p.18 are given rates of working expenses: cream and seed or olive oil. Lines 3, 5, 6. Face: cream —5 g; oil—7 g.

Lines 17–19. Neck: cream—3 g; oil—5 g.

For the proposed massage of the face and neck are used the following creams:>>Yantar>>(Amber),>>Lux>>, >>Beriozka (Bearch) ,<<Massage emulsion>>(Germany).(p.18, 1.23, 24).

I. I. Kolgunenko <<The Lessons of Beauty>>, 3rd edition, Kiev, >>Reklama>>, 1980.

In the section << Everybody has to know about massage but to perform it only a specialist>> is told about the aims of the massage and preparation of the face and neck for it (pp.14, 15, 16). In conclusion (p.16, 1.20–23) the author writes: << Massage has to calm, blow a dream and if a patient is dreamed it means the massage is carried out properly.>>

There are written the section << The hygienic (prophylaxis) extenuating massage of the face (FIG. 2) what is the surface mechanical irritant, its action is directed on the skin and mimic muscles of the face with the aim to prevent the premature aging of the soft tissues, formation of the early wrinkles and softening of the extremely dry, rough, weather-beaten skin.>>(p. 16, 1.24–34).

The massage is performed with calm, unhurried rhythmical surface movements strictly on the skin lines, with both hands simultaneously; and a requirement of the rhythm is the necessary one (4 time), without any shifting and tension of the face skin>>( p. 16, 1.9–15). At the base of this kind of massage lies different pressings with vibration (or without) and grappled stroking movements also.

This kind of massage is performed on the massage oil (compound from 30 g vegetable oil and 20 g liquid paraffin (as an alternative oil is a castor oil) or on massage cream. The length of one treatment is 8–10 minutes>>(p.18, 1.19–13).

Description of the technique of the massage movements is shown on pages 18, 19 and 20.

<<Therapeutic massage of the face just as hygienic is a surface mechanical irritant, its action is directed mostly to the skin and mimic muscles>>(p.21, 1.4–9).

At the base of it are movements of straight pressing stroking, that have to be like dotted line: after each pressure inward, to bone needs gently to lift and weaken shifting hands>> (p.21,1.37–42)

<< At the straight pressing interrupting stroking each pressure is performed deeply with some force. When you begin feeling a bone with your fingers it will be the limit of that force. Between two pressures hands are moved without any forces and pressure on the skin. Every small transversal pressing pressure is performed as slow energetic pressures inward, on subcutaneous tissues. After each pressure needs to lift fingers and then energetically weaken them.>>(p. 21,1.5–18). Movements are performed 4 time. <<This kind of massage acts on individual tracts of wrinkles situation>> (p.21, 1.23–24). <<This treatment uses the massage oil (of the same compound as above- mentioned) or massage cream. The duration of the session is 12–15 minutes.>> (p. 21, 1.53, 54, 1, 2, 3, 4). Then on p.22 is shown the description of the technique of movements. <<Therapeutic plastic massage with vibrations for the face is a deep mechanical irritant (FIG. 4), its action is directed to the skin of the facial muscle and its nerve-receptor apparatus, sudoriferous and sebaceous glands, muscles of the face, subcutaneous fatty layer>> etc. (p.23,1.18–24).

<< The main movements, that are used in this kind of massage are volumetrical, deep, pressing pressures with vibration, directed inward of the tissues and shallow transversal pressures without vibration with the same direction>>

(p.23, p.54, 55, 1–5) Movements are carried out with both hands 4 time (p.23, 1.10–12) and pressures have to be calm and slow (p.23,1.5–6).

<< The force of pressures is correct if each contraction of muscle is alternated with full weakening of hands>> (p. 24,1.16–19).

This kind of massage is performed with dry massage agents—talcum, spirit or cleaned, fatless skin. The length of one treatment is 8–10 minutes (p.24, 1.28–23).

Technique of movements is shown on pages 24, 25, 26.

<< Softening massage of the front-lateral surfaces of the neck is directed on the skin and mimic muscles of the neck, but partially on the deeper tissues layers of the chin tract and upper part of the neck.>>(p. 26, 1.3–8).

<<The base of this kind of massage are rhythmic (4 time), slow, mostly surfaced slapping of external surface of the hand, straight pressing stroking, small transversal pressing pressures and fixing vibration.>>(p. 26, 1.30–37).

The process of slapping is performed in that way, that << a shock should be executed with the whole back of the hand, what is placed on the face (chin tract), caving in that way <<to clasp>> its down part. After every shock hands are stopped for several seconds as have been set at one place, clasp the tissues, press up and inward, pressing them to bones and then gently are taken from the down part of the face and weaken completely. Then again follows a shock and so on. Each shock alternates with calmness. During this process are used fat massages agents.>> (p. 27, 1.1–17).

There is a description of the movements on pages 27, 28.

The comparative analysis of above-mentioned publications Summarizing materials of these publications we can say, that all modem methods of massage (except the massage, proposed by Mrs. I. I. Kolgunenko) are directed at the change of the skin surface with improvement of the skin feeding but not at the deep aging changes of the muscular and ligamental apparatus. In cosmetology mostly are used hygienic cosmetic massage, at the base of it are the surface measured smooth movements, what are performed in accordance with direction of the massage lines. Preliminary on the skin are put one or another massage agent in a small amount. Massage is carried out with light, soft movements 4 time (on the individual parts of the skin—8 time). The length of one session of hygienic massage is 15–20 minutes, the whole cycle of such massage is 10–20 procedures.

Therapeutic massage is prescribed when a patient suffers with some kind of disease (nervous, disturbance of circulation of the blood or fat removing, blackhead rash etc.). It is carried out generally more energetically in comparing with hygienic massage. There are several kinds of therapeutic massage: plastic massage on Mr. Pospelov's scheme, massage on Jacque's scheme.

From the Kolgunenko's method the claimed massage is differed as follows:

1. All movements are performed continuously with putting of plentiful quantity of cream and vegetable oil on the skin;
2. Speed of all movements overcomes frequency of them in 3-3,5 times in comparing with all other methods, including the Kolgunenko's one;
3. The length of one session lasts longer in 6 times;
4. The Kolgunenko' method means the joining of all subcutaneuos tissues, the claimed massage helps not only to join subcutaneous tissues but burning up to possible minimum the subcutaneous fat, muscle tissue and after that minimum of the muscle tissue has achieved—attachment of the muscles to skeleton;
5. In this method using special cream—suspension and vegetable oil are natural solvents of neutral fats, they remarkably accelerate its solution and withdrawal, intensify the process of regeneration of metabolism.

The plastic Kolgunenko's method is performed on the dry face.

My claimed information is concerned to plastic massage.

The essence of plastic massage is in deeper mechanical action on not only the skin and mimic muscles of the face and neck, but on the subcutaneous fat cellular tissue, blood and lymphatic vessels.

The aim of plastic massage is not a prevention, but treatment of signs of aging.

The claimed method proposes to carry out courses of massage from the young age, when there has already the obvious changes in the muscle itself, subcutaneous tissues and shifting of the skin. Thus the claimed method is directed not at improvement of the surface of the skin, but at the deep change of the muscular and ligamental apparatus. The present method proposes reduction of the subcutaneous fatty layer to a minimum, acceptable level, recovery of the elasticity of the muscular and ligamental apparatus and as a result of this removal surplus of the skin not by cutting it off, but as a result of its natural tightening. Besides of it there is the essential decreasing of the muscle mass of the face. At the end of the course all muscles are pull on the scull, fastened at definite place on it and then merged in integral monolyth structure. Actually the attained effect is comparable with the <<shaping>> effect for the face.

All details of my method are noted in the Application (pages 4, 5, 6, 7 and 8). In addition to what was said above, I can note that all movements are performed continuously with plentiful quantity of vegetable oil and cream. Supporting sessions, what are used according to other methods by 3–4 times a month, are excluded at application of my method.

What is claimed is:

1. A method of massaging the face and neck, consisting of applying a massage agent on the skin and subsequently stroking and spirally rubbing and slapping with the palm surface of the end phalanxes of the 2nd–4th fingers, taking the anatomicophysiological location of the muscles and ligamental apparatus of the soft tissues of the face and neck into account, characterized in that the rubbing and slapping are carried out until a stop is felt in the tissues of the face and neck, the rate of carrying out the rubbing and slapping movements is equal to 200–250 movements per minute, the total number of movements for treatment of each muscle is 3000–4000, the length of carrying out one treatment is 1 hour 20 minutes, the palm surfaces of all the fingers and the palms of both hands participate in the movements.

2. The method of claim 1, wherein the massage agent is a cream for massage comprising cacao oil, lanolin, wax, oil solutions of vitamins A and E, vegetable oil and water, characterized in that it additionally comprises citric acid, said vegetable oil is olive or seed oil, said wax is beeswax, wherein the ratio of the ingredients, as a percentage by weight, is the following:

| | |
|---|---|
| CaCao Oil | 4–6 |
| lanolin | 3–5 |
| Beeswax | 3–4 |
| Vitamin A in Oil | 0.8–1.2 |
| Vitamin E in Oil | 0.8–1.2 |
| Citric Acid | 0.8–1.2 |
| Olive or Seed Oil | 30–50 |
| Distilled Water | balance to 100%. |

3. A cream for massage, including cacao oil, lanolin, wax, oil solutions of vitamins A and E, vegetable oil and water, characterized in that it additionally comprises citric acid, the vegetable oil is olive or seed oil, the wax is beeswax, with the ratio of the ingredients, % by weight:

| | |
|---|---|
| Cacao oil | 4–6 |
| lanolin | 3–5 |
| Beeswax | 3–4 |
| Vitamin A in oil | 0.8–1.2 |

-continued

| | |
|---|---|
| Vitamin E in oil | 0.8–1.2 |
| Citric acid | 0.8–1.2 |
| Olive or seed oil | 30–50 |
| Distilled water | balance. |

* * * * *